(12) United States Patent
Kato et al.

(10) Patent No.: US 8,097,640 B2
(45) Date of Patent: *Jan. 17, 2012

(54) PROPHYLACTIC OR THERAPEUTIC AGENT FOR DIABETIC MACULOPATHY

(75) Inventors: Noriaki Kato, Nagoya (JP); Hiroshi Nagano, Nagoya (JP); Kaori Taniko, Nagoya (JP); Takahito Jomori, Nagoya (JP)

(73) Assignee: Sanwa Kagaku Kenkyusho Co., Ltd., Nagoya-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/842,391

(22) Filed: Jul. 23, 2010

(65) Prior Publication Data

US 2010/0305177 A1  Dec. 2, 2010

Related U.S. Application Data

(63) Continuation of application No. 10/587,320, filed as application No. PCT/JP2005/001187 on Jan. 28, 2005, now Pat. No. 7,910,615.

(30) Foreign Application Priority Data

Jan. 30, 2004  (JP) ................... 2004-022547

(51) Int. Cl.
    *A01N 43/50* (2006.01)
(52) U.S. Cl. ........................................ 514/389
(58) Field of Classification Search .................. None
    See application file for complete search history.

(56) References Cited

U.S. PATENT DOCUMENTS

| 4,740,517 A | 4/1988 | Kurono et al. |
| 5,639,482 A | 6/1997 | Crary |
| 6,426,341 B1 | 7/2002 | Mylari |
| 6,479,729 B1 | 11/2002 | Campochiaro et al. |

FOREIGN PATENT DOCUMENTS

| JP | 61-200991 A1 | 9/1986 |
| JP | 07-242547 A1 | 9/1995 |
| JP | 0 719 556 A2 | 7/1996 |
| JP | 08-231549 A1 | 9/1996 |
| JP | 1 106 210 A2 | 6/2001 |

OTHER PUBLICATIONS

Speicher, Matthew a. et al., "*Pharmacologic Therapy for Diabetic Retinopathy*," Expert Opinion on Emerging Drugs, vol. 8, No. 1 (2003), pp. 239-250.
Masahiko Akita et al., "*Effects of and Aldose Reductase Inhibitor, SNK-860, on the Histopathological Changes of Retinal Tissues in a Streptozotocin-Induced Rat Model*," Acta Med. Okayama, vol. 47, No. 5 (1993), pp. 299-304.
Irina G. Obrosova et al., "*Aldose Reductase Inhibitor Fidarestat Prevents Retinal Oxidative Stress and Vascular Endothelial Growth Factor Overexpression in Streptozotocin-Diabetic Rats*," Diabetes, vol. 52, No. 3 (2003), pp. 864 to 871.
Giebel, S.J. et al., "*Upregulation of Extracelluar Proteinases and Angiopoietin 2 during Blood-Retinal-Barrier Alteration in the Diabetic Rat Model*," ARVO Annual Meeting Abstract Search and Program Planner, vol. 2003, pp. Abstract No. 3903.
Sima, J. et al., "*Angiostatin Decrease Vascular Leakage by Down-Regulating VEGF Expression*," ARVO Annual Meeting Abstract Search and Program Planner, vol. 2003, pp. Abstract No. 363.
Lopes de Faria et al., Acta Ophthalmol Scand, 77, p. 170-175, 1999.
Definition of "prevent" from dictionary.com, accessed Nov. 28, 2007.
Wani et al., JK Practitioner 10(4):275-278, 2003.
MacGregor, Leslie C., et al. "*Experimental Diabetes Mellitus Impairs the Function of the Retinal Pigmented Epithelium*," Metabolism, vol. 35, No. 4, Suppl. 1 (Apr. 1986), p. 28-34.
Ferris III, Frederick L., "*Foreword: Evaluation of New Treatment Paradigms for Diabetic Retinopathy and Macular Edema*," Survey of Ophthalmology, vol. 47, Suppl. 2 (Dec. 2002), p. S237.
Definition of Maculopathy from Medicinenet.com, accessed Sep. 2, 2008.

*Primary Examiner* — Nissa Westerberg
(74) *Attorney, Agent, or Firm* — Burr & Brown

(57) ABSTRACT

A prophylactic or therapeutic agent for diabetic maculopathy, which can be administered for a long time and exhibits efficacy in a mechanism different from that of existing medicines. The invention relates to a prophylactic or therapeutic agent for diabetic maculopathy, comprising, as an active ingredient, a compound represented by the general formula:

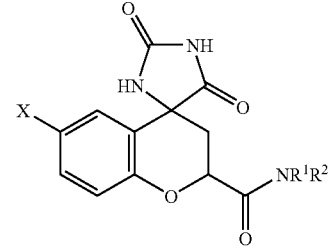

wherein X represents a halogen or a hydrogen atom, $R^1$ and $R^2$ concurrently or differently represent a hydrogen atom or an optionally substituted C1 to C6 alkyl group, or $R^1$ and $R^2$, together with a nitrogen atom bound thereto and optionally another nitrogen atom or an oxygen atom, are combined to form a 5- to 6-membered heterocycle. Preferably, the compound is (2S,4S)-6-fluoro -2',5'-dioxospiro chroman-4,4'-imidazolidine]-2-carboxamide. The invention also provides a model animal with diabetic maculopathy produced by subjecting a diabetic animal to intraocular ischemia/reperfusion to express edema in a retinal visual cell layer or in a macula lutea.

6 Claims, 5 Drawing Sheets

PROPHYLACTIC OR THERAPEUTIC AGENT FOR DIABETIC MACULOPATHY

CROSS-REFERENCE TO RELATED APPLICATIONS

This application is a continuation of U.S. application Ser. No. 10/587,320, filed May 10, 2007, issued as U.S. Pat. No. 7,910,615 which is the National Phase of International Application No. PCT/JP2005/001187 having an international filing date of Jan. 28, 2005, and claims the benefit of Japanese Application 2004-022547, filed Jan. 30, 2004, the entireties of which are incorporated herein by reference.

BACKGROUND OF THE INVENTION

1. Field of the Invention

The present invention relates to a new use of a hydantoin derivative, in particular, (2S,4S)-6-fluoro-2',5'-dioxospiro[chroman-4,4'-imidazolidine]-2-carboxamide, as a pharmaceutical preparation.

2. Description of the Related Art

The number of patients with diabetes mellitus as a life style-related disease is increasing, and in a survey on diabetes mellitus in 2002 conducted by the Ministry of Health, Labor and Welfare, the number of patients with diabetes mellitus in Japan is estimated to be 7.4 millions. In a recent epidemiological study on 913 cases of non-insulin-dependent diabetes mellitus, about 8% (about 600,000 patients) of patients with diabetes mellitus are reported to have maculopathy. It is estimated that as the number of patients with diabetes mellitus increases, the number of patients with diabetic maculopathy also increases.

Diabetic maculopathy, together with diabetic retinopathy, is considered to be important as one of the retinal diseases inpatients with diabetes mellitus. Diabetic maculopathy is classified into macular edema, ischemic maculopathy, retinal pigment epitheliopathy and macular traction. The object of diabetic retinopathy therapy is to prevent blindness (loss of visual acuity), while the object of diabetic maculopathy therapy is to prevent and ameliorate deterioration of visual acuity. Macula lutea are significantly different in form from retinas so as to attain high central visual acuity (sharpest and high visual acuity), and have a special structure (absent from an inner plexiform layer and an inner nuclear layer) with extremely fewer tissues other than visual cells. Accordingly, the clinically problematic deterioration of visual acuity is due to maculopathy. A development of photocoagulation and vitrectomy made it possible to almost prevent blindness attributable to retinopathy, but is not satisfactory for maculopathy, so a therapy that is different from retinopathy therapy is needed for maculopathy. This is also important in light of the treatment of many patients having maculopathy only without having retinopathy. Especially, a recent increase in pan-photocoagulation for diabetic retinopathy is estimated to worsen macular edema in diabetic maculopathy, to cause further deterioration of visual acuity. Accordingly, the main point of therapy is shifting toward improvement of quality of life (QOL) of patients by maintaining and improving visual acuity.

Macular edema caused by breakage of a blood-retinal barrier in a retinal vascular endothelial cell or a retinal pigment epithelial cell accounts for about 90% of maculopathy and is a major cause for deterioration of visual acuity in maculopathy. This deterioration of visual acuity does not lead to blindness, but causes extreme deterioration of visual acuity referred to as social blindness making usual living difficult. On one hand, the average life span increases due to the advancement of medical technology, and thus, such a deterioration of visual acuity is a serious problem that cannot be neglected in consideration of QOL. Major therapy conducted for preventing or ameliorating deterioration of visual acuity includes photocoagulation, vitrectomy and chemotherapy. Under the present circumstances, photocoagulation and vitrectomy are examined for their effectiveness in clinical studies, and the effectiveness and safety for macular edema have still not been established. There are cases where complications of neovascular glaucoma and worsening edema occur, and thus, there is an earnest desire for the advent of an effective and safe chemotherapy. In the present chemotherapy, steroids and carbonate dehydratase inhibitors with anti-inflammatory action as major efficacy are used in symptomatic therapy, but their effectiveness is not established and their administration over a long period of time leads to the occurrence of side effects, and thus, the continuous use thereof in chronic diseases such as diabetes mellitus is not desirable under the present circumstance.

(2S,4S)-6-Fluoro-2',5'-dioxospiro[chroman-4,4'-imidazolidine]-2-carboxamide (hereinafter, referred to as SNK-860) found by the present applicant was developed as a compound which has a strong inhibitory activity on aldose reductase and is highly safe even in administration for a long time, and clinical test thereof as a therapeutic agent for diabetic neuropathy is advancing worldwide at present.

With respect to hydantoin derivatives including SNK-860, the use thereof for diabetic neuropathy is described in JP-A 61-200991 (1986), the use thereof for diseases in circulatory organs in JP-A 04-173791 (1992), the use thereof for various diseases accompanying aging in JP-A 06-135968 (1994), the use thereof for simple diabetic retinopathy in JP-A 07-242547 (1995), and the use thereof for diabetic keratopathy in JP-A 08-231549 (1996). However, the effectiveness of the hydantoin derivatives for diabetic maculopathy has not been reported.

As described above, establishing an effective and highly safe therapy for treating diabetic maculopathy is strongly desired in the medical field. Under the present circumstances, the advent of a highly safe chemotherapy enabling administration over a long time period is strongly desired because of the safety problems associated with treatment by opthalmologic operation. However, heretofore, there has been no model for evaluating experimental diabetic maculopathy, which is important for the development of such therapeutic agents, and the establishment of an experimental model for development of pharmaceutical preparations is an urgent task.

SUMMARY OF THE INVENTION

The present invention has been made in consideration of the drawbacks associated with the prior art as described above, and an object of the present invention is to provide a prophylactic or therapeutic agent for treating diabetic maculopathy, which can be administered over a long period of time which and exhibits efficacy in a mechanism different from that of existing medicines, as well as an experimental animal model which can be used in the evaluation of medicines for diabetic maculopathy.

The present inventors first sought to establish an experimental animal model for diabetic maculopathy. That is, simplicidentata such as rats have no macula lutea, and there is no report on edema at a site outside of a retina such as a visual cell layer, that is, at a site corresponding to macula lutea, and whether its severeness is increased or decreased by diabetes mellitus is not reported either. Accordingly, the present inventors studied its pathologic condition using an animal, and as a result we found that when a diabetic rat was allowed to be in an intraocular ischemic state and then subjected to reperfusion, edema was expressed on a visual cell layer. In this experimental model, it is suggested that an increase in oxidation stress, such as excessive production of free radicals occurring in the eye by ischemia and reperfusion, promotes vascular permeability by breaking an inner blood-retinal barrier (barrier regulating the transfer of a substance from a retinal blood vessel to the outside of the blood vessel) and an outer blood-retinal barrier (barrier regulating the transfer of a substance from a choroid to retina). Accordingly, it is estimated that the edema was expressed by this promotion of vascular permeability in addition to the promotion of retinal vascular permeability by diabetes mellitus. The present model thus expressing edema in the visual cell layer has an onset mechanism very similar to that of macular edema in human diabetic maculopathy and can be said to be a model suitable for the evaluation of diabetic maculopathy.

The present inventors also examined whether or not edema was expressed in a macula lutea in a diabetic monkey by using an evaluation system established in rats. As a result, it was confirmed that edema is observed in a macular central fovea participating most in central visual acuity. This can be said to further evidence that the edema-expressing model established in a rat is suitable in evaluation of diabetic maculopathy.

When the present inventors used the above-mentioned experimental model to evaluate SNK-860, the inventors discovered that SNK-860 is effective for edema in a retinal visual cell layer having a central role in maintaining visual acuity or for edema in a macula lutea (particularly macular central fovea). By conducting further clinical evaluations, the present inventors discovered that the compound is not only effective for treating edema in a macula lutea, but also exhibits an effect of improving visual acuity. That is, the present invention relates to a prophylactic or therapeutic agent for treating diabetic maculopathy, which comprises, as an active ingredient, a hydantoin derivative represented by the following general formula, preferably (2S,4S)-6-fluoro-2',5'-dioxospiro [chroman-4,4'-imidazolidine]-2-carboxamide (SNK-860)

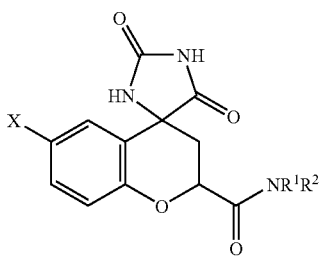

(In the formula, X represents a halogen or a hydrogen atom, $R^1$ and $R^2$ concurrently or differently represent a hydrogen atom or an optionally substituted C1 to C6 alkyl group, or $R^1$ and $R^2$, together with a nitrogen atom bound thereto and optionally another nitrogen atom or an oxygen atom, are combined to form a 5- to 6-membered heterocycle, and the halogen represented by X is preferably fluorine, and the C1 to C6 alkyl group is preferably a methyl group.)

Examples of the diabetic maculopathy include macular edema and retinal pigment epitheliopathy. Examples of the diabetic macular edema include local macular edema and diffuse macular edema. The prophylactic or therapeutic agent for diabetic maculopathy according to the present invention is preferably in the form of an oral agent.

The present invention also relates to an experimental animal model with diabetic maculopathy, which uses an animal such as simplicidentata or primates other than humans. This is an animal model with diabetic maculopathy that is produced by subjecting a diabetic animal to intraocular ischemia/reperfusion to express edema in a retinal visual cell layer or in a macula lutea (particularly in macular central fovea). As the animal with diabetes mellitus, it is possible to use not only animals having diabetes mellitus induced for example by administering a pharmacological agent such as streptozotocin or alloxan into a rat (normal rat) or a monkey (normal monkey), but also animals with hereditary diabetes mellitus.

Further, the present invention encompasses a method of evaluating a pharmacological agent for diabetic maculopathy, which comprises using the model animal described above. That is, the method of the present invention is a method of evaluating the effectiveness of a pharmacological agent on edema, which comprises administering a pharmacological agent to be evaluated into the model animal and measuring the thickness of a retinal visual cell layer or the thickness and/or volume of a macula lutea.

The present invention provides not only a therapeutic agent for diabetic maculopathy, which can be administered over a long period of time, but also an experimental animal model that is needed in order to conduct research to discover a therapeutic agent for diabetic maculopathy.

BRIEF DESCRIPTION OF THE DRAWINGS

In FIG. 1, the asterisk indicates that there is a significant difference with a risk factor of 5%.

In FIG. 2, the asterisk indicates that there is a significant difference with a risk factor of 5%.

In FIG. 3, the asterisk indicates that there is a significant difference with a risk factor of 5%.

DETAILED DESCRIPTION OF THE INVENTION

Figure 1:
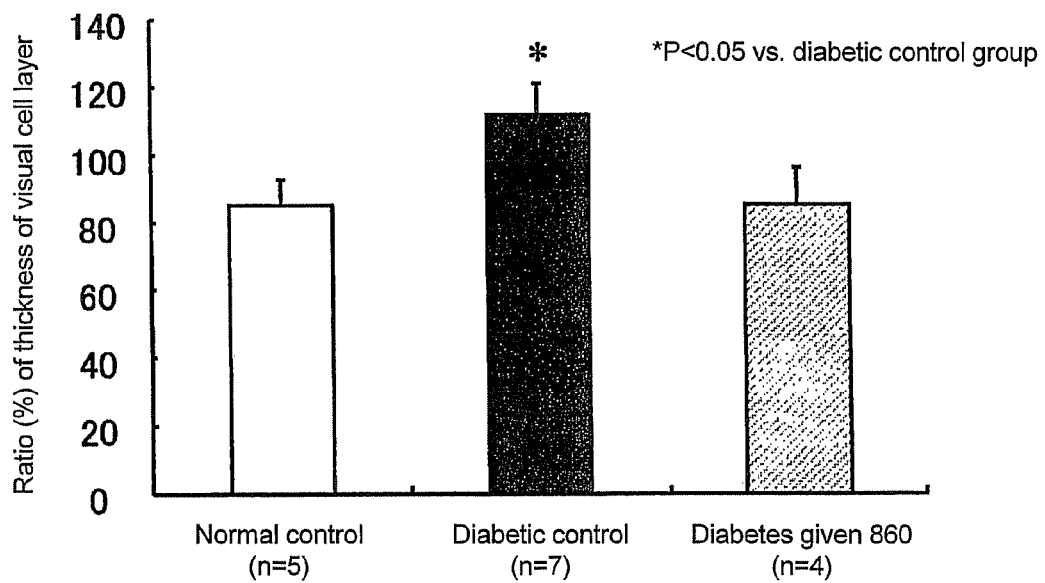
FIG. 1 shows the ratio of the thickness of a retinal visual cell layer (ratio (%) of the thickness of a visual cell layer in an ischemic/re-perfused eye/the thickness of a visual cell layer in an untreated eye in the same individual) in Efficacy Pharmacological Test Example 1.

Hereinafter, the present invention is described in more detail.

Hydantoin derivatives (particularly SNK-860) can be orally administered for example as tablets, capsules, powder, granules, liquid or syrup or parenterally as an injection and suppositories, which were formed by usual pharmaceutical manufacturing techniques. Pharmaceutically acceptable excipients in pharmaceutical manufacturing, for example starch, lactose, refined white sugar, glucose, crystalline cellulose, carboxy cellulose, carboxymethyl cellulose, carboxyethyl cellulose, calcium phosphate, magnesium stearate and gum arabic can be used in the solid preparation, and if necessary a lubricant, a binder, a disintegrating agent, a coating agent, a coloring agent etc. can be incorporated into the solid preparation. In the liquid preparation, a stabilizer, a solubilizer, a suspending agent, an emulsifying agent, a buffer agent, a preservative etc. can be used. The dose varies depending on symptoms, age, administration method, preparation form etc., but preferably the compound described above is administered usually in the range of 1 to 200 mg, preferably 1 to 100 mg, into an adult all at once or in divided portions per day for consecutive days.

In the model animals with diabetic maculopathy according to the present invention, animals with diabetes mellitus by treating normal animals with a pharmacological agent such as streptozotocin (STZ), or alloxan or animals with hereditary diabetes mellitus, can be used as diabetic animals. As the type of the animals, simplicidentata such as rats, nonhuman primates such as monkeys, duplicidentata such as rabbits, and carnivorous animals such as canines can be used.

When the simplicidentata, duplicidentata or carnivorous animals that inherently do not have macula lutea are used, edema is expressed in a retinal visual cell layer and the thickness of the retinal visual cell layer can be used in evaluation. In the nonhuman primates, on the other hand, there are usually macula lutea, so edema is expressed in a macula lutea and the thickness and/or volume of the macula lutea is used in evaluation. The thickness etc. of the macula lutea are evaluated preferably in the site of macular central fovea. Intraocular ischemia/reperfusion treatment can be easily carried out by stopping a retinal blood stream by increasing the intraocular pressure and then relieving the intraocular pressure to allow reperfusion. The thickness of the retinal visual cell layer or the macula lutea varies significantly depending on individuals, so a treated eye and untreated eye are set preferably in the same individual by subjecting only one eye to intraocular ischemia/reperfusion treatment. By so doing, the relative evaluation of "thickness of a treated eye/thickness of an untreated eye" can be carried out on the basis of the untreated eye in each animal.

A pharmacological agent to be examined is administered into the model animal with diabetic maculopathy according to the present invention and then evaluated for the effectiveness of the pharmacological agent for edema as described above, whereby the effectiveness of the pharmacological agent for diabetic maculopathy can be evaluated. The method of administering the pharmacological agent is not particularly limited, and administration of the pharmacological agent is also carried out after intraocular ischemia/reperfusion treatment thereby clarifying the therapeutic effect.

EXAMPLES

Efficacy Pharmacological Test Example 1

Rat Test 1

1. Test Method

Diabetes mellitus was induced in male Sprague Dawley rats (8-week-old) weighing about 250 g by injecting streptozotocin (STZ manufactured by Sigma) intravenously into their tail at the dose of 60 mg/kg. One week after the treatment with STZ, serum glucose was measured, and rats with at least 300 mg/dl glucose were then used in the experiment as diabetic rats. The set groups were the following 3 groups, and after 2 weeks after the treatment with STZ, 5% gum arabic solution or SNK-860 solution was orally administered once a day.

(1) Normal control group (5 rats): Given 5% gum arabic solution in a ratio of 5 ml/kg.
(2) Diabetic control group (7 rats): Given 5% gum arabic solution in a ratio of 5 ml/kg.
(3) Diabetic group given 32 mg/kg SNK-860 (4 rats): Given a suspension of SNK-860 (32 mg/5 ml) in 5% gum arabic solution in a ratio of 5 ml/kg.

After administration for 2 weeks, intraocular ischemia was caused by the treatment described below. After the treatment was finished, the animals were maintained as usual for 2 days, and thereafter, the eyeballs were excised and histologically evaluated. Administration of the pharmacological agent was also conducted for a period (2 days) of reperfusion after ischemic treatment.

Retinal Ischemia by Increasing the Intraocular Pressure

A drip infusion set (Terufusion Drip Infusion Set manufactured by Terumo) was connected to a bottle containing an intraocular perfusion solution (Opeguard MA manufactured by Senjyu Seiyaku), and an extension tube (Terumo) to which a three-way stopcock had been attached was connected thereto. A needle (30 G×½, manufactured by Nippon Becton Dickinton) was fitted to the end of the tube. The bottle containing an intraocular perfusion solution was fixed to a certain height with a stand. The rats were anesthetized by administering sodium pentobarbital (Somunopentyl manufactured by Schering-Plough Animal Health) intraperitoneally in a ratio of 50 mg/kg, and then a mydriatic (Mydrin P manufactured by Santen Pharmaceutical) and a local anesthetic (Benoxyl eye drop 0.4%, Santen Pharmaceutical) were dropped onto the right eye. The anesthetic was additionally administered when necessary. Thereafter, a needle was stuck into an anterior chamber of the rat right eye and the intraocular pressure load was performed by manipulating the three-way stopcock (the intraocular pressure was increased to 130 mmHg or more for 60 minutes). Because the ocular fundus in the Sprague Dawley rat turns from red to white by stopping the retinal blood stream by increasing the intraocular pressure, achievement of retinal ischemia can be easily observed. After the intraocular pressure was increased for the predetermined time, the needle was removed to relieve the intraocular pressure to allow reperfusion, and an antibacterial eye drop (tarivit eye ointment manufactured by Santen Pharmaceutical) was applied onto the right eye.

Histological Evaluation

Two days after the ischemia treatment (two days after the reperfusion), the rat left and right eyeballs were excised under anesthesia with ether. The excised eyeballs were placed in an ice-cold fixing solution (phosphate buffer solution containing 3% glutaraldehyde) and fixed therein for 2 days. Thereafter, the eyeballs were washed for 1 day with a phosphate buffer solution. The eyeballs were embedded in a usual manner into paraffin to prepare a transverse section containing a bundle of optic nerves. The section was stained with hematoxylin-eosin. The histological evaluation was conducted by each of two (2) visual fields in left and right side (4 visual fields/rat) in the vicinity of the bundle of optic nerves, from an optical microscope to an image analyzer (IPAP-WIN, Sumika Techno Service).

In each of the resulting retinal images, the thickness of the visual cell layer was measured. The degree of edema was expressed in percentage by dividing the thickness of the visual cell layer of the ischemic/re-perfused eyeball (right eye) by the thickness of the visual cell layer of the untreated eyeball (left eye) in the same individual. As an indicator of retinal cell functions, nuclei in the inner retinal layer (ganglion cell layer) were counted, and the degree of loss of nuclei was evaluated relative to the ratio of the number of nuclei occurring per unit area.

2. Results and Discussion

The effect of SNK-860 on edema is shown in FIG. 1. The thickness of the visual cell layer after ischemia/reperfusion in the rats in the normal control group was reduced as compared with that of the untreated eye. On the other hand, the rats in the diabetic control group showed an increase in the visual cell layer by ischemia/reperfusion, and formation of edema was confirmed ($p<0.05$). In the diabetic group given 32 mg/kg SNK-860, the thickness was almost the same as that of the normal control group, and no edema was observed.

Next, loss of nuclei from ganglion cells is described. As a result of examination of the degree of loss of nuclei from cells, no loss of nuclei was recognized in 5 rats in the normal control group. In the diabetic control group, evident loss of nuclei occurred in 3 of 7 rats, among which 2 rats showed loss of 50% or more nuclei. In the diabetic group given 32 mg/kg SNK-860, loss of nuclei was not observed in all 4 rats.

These results reveal that SNK-860 inhibits edema formation under diabetes in a visual cell layer and also prevents disturbances in functions of retinal cells.

Efficacy Pharmacological Test Example 2

Rat Test 2

1. Test Method

The test was carried out in accordance with Efficacy Pharmacological Test Example 1. The set groups were the following 4 groups, and from 2 weeks after the treatment with STZ, 5% gum arabic solution or SNK-860 solution was orally administered once a day.
(1) Normal control group (10 rats): Given 5% gum arabic solution in a ratio of 5 ml/kg.
(2) Diabetic control group (9 rats): Given 5% gum arabic solution in a ratio of 5 ml/kg.
(3) Diabetic group given 2 mg/kg SNK-860 (10 rats): Given a suspension of SNK-860 (2 mg/5 ml) in 5% gum arabic solution in a ratio of 5 ml/kg.
(4) Diabetic group given 32 mg/kg SNK-860 (9 rats): Given a suspension of SNK-860 (32 mg/5 ml) in 5% gum arabic solution in a ratio of 5 ml/kg.

Retinal ischemia produced by increasing the intraocular pressure was in accordance with Efficacy Pharmaceutical Test Example 1. Histological evaluation was also in accordance with Efficacy Pharmaceutical Test Example 1.

2. Results and Discussion

Figure 2:
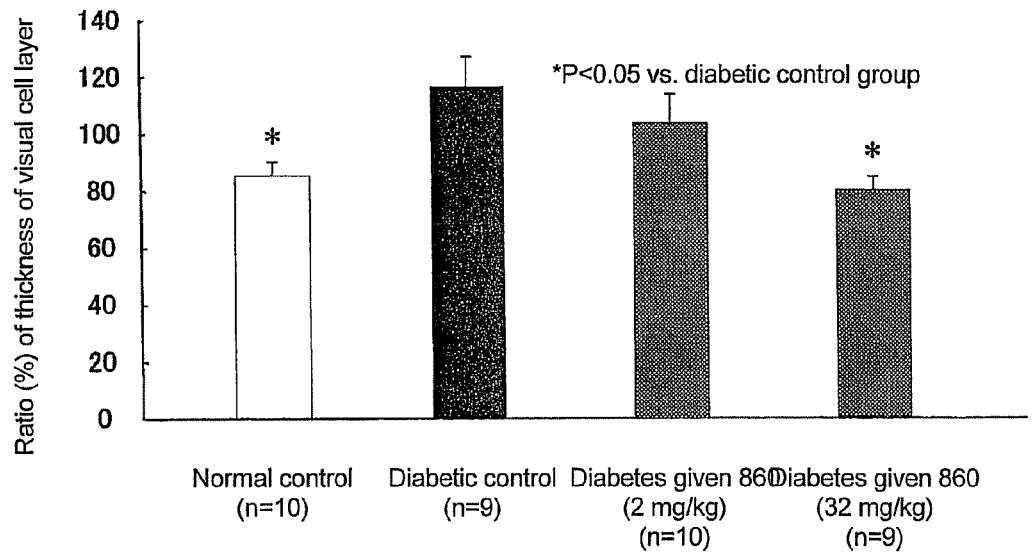
FIG. 2 shows the ratio of the thickness of a retina visual cell layer (ratio (%) of the thickness of a visual cell layer in an ischemic/re-perfused eye/the thickness of a visual cell layer in an untreated eye in the same individual) in Efficacy Pharmacological Test Example 2.

The effect of SNK-860 on edema is shown in FIG. 2. The thickness of the visual cell layer after ischemia/reperfusion in the rats in the normal control group was reduced as compared with that of the untreated eye. On the other hand, the rats in the diabetic control group showed an increase in the visual cell layer by ischemia/reperfusion, and formation of edema was confirmed ($p<0.05$). In the diabetic group given 2 mg/kg SNK-860, no inhibitory action on edema was observed, but in the diabetic group given 32 mg/kg SNK-860, the thickness of the visual cell layer was kept in the same value as in the normal control group, and an evident inhibitory action on edema was observed. These results indicate that edema formation under diabetes in a visual cell layer is inhibited by administration of a high dose of SNK-860.

Efficacy Pharmacological Test Example 3

Monkey (*Macaca fascicularis*) Test

1. Method

Diabetes mellitus was induced in male monkeys (*Macaca fascicularis*) (3-year-old) weighing about 2.1 to 2.4 kg by intravenously injecting STZ into their foreleg vein at the dose of 80 mg/kg. Two days after the treatment with STZ, blood glucose level was measured, and monkeys with at least 200 mg/dl glucose were then used in the experiment as diabetic monkeys. Insulin was administered subcutaneously once or twice per day into monkeys showing a blood glucose level of 300 mg/dl. The set groups were the following 3 groups, and from 2 weeks after the treatment with STZ, 5% gum arabic solution or SNK-860 solution was orally administered once a day.
(1) Normal control group (4 monkeys): Given 5% gum arabic solution in a ratio of 5 ml/kg.
(2) Diabetic control group (6 monkeys): Given 5% gum arabic solution in a ratio of 5 ml/kg.
(3) Diabetic group given 32 mg/kg SNK-860 (4 monkeys): Given a suspension of SNK-860 (32 mg/5 ml) in 5% gum arabic solution in a ratio of 5 ml/kg.

After administration for 2 weeks, intraocular ischemic treatment was carried out as described below, and after the treatment was finished, the animals were maintained as usual for 7 days. Before the ischemic treatment and 7 days after treatment, the thickness and volume of the macular central fovea (in the diameter range of 1 mm from the center of the macula lutea) were measured by an OCT scanner (Stratus OCT, Carl Zeiss). Administration of the pharmacological agent was also conducted for the period (7 days) of reperfusion after the ischemic treatment.

Retinal ischemia produced by increasing intraocular pressure was in accordance with Efficacy Pharmaceutical Test Example 1. However, the size of the needle used was 25 G×½ (Terumo). After a mydriatic (Mydrin P manufactured by Santen Pharmaceutical) was dropped onto the right eye, the monkey was anesthetized by intramuscularly administering ketaral (Sankyo Life Tech). Subsequently, a local anesthetic (Benoxyl eye drop 0.4%) was dropped onto the eye, and the monkey was prevented from blinking with an eyelid speculum. Anesthesia with ketaral was additionally carried out when necessary.

The thickness and volume of the macular central fovea were measured in the following manner. After a mydriatic (Mydrin P) was dropped onto the right eye of the monkey to dilate the pupil of the eye sufficiently, the monkey was anesthetized by intramuscularly administering Ketaral. Thereafter, the monkey was allowed to sit on a monkey chair and the head was fixed. The inside of the eye was observed with an OCT scanner to identify the macula lutea, followed by scanning. On the basis of the resulting cross-sectional macular image, the thickness and volume of the macular central fovea were analyzed.

TABLE 1

| Group | Number of monkeys | Average macula lutea thickness (μm) | | Average macula lutea volume (mm³) | |
|---|---|---|---|---|---|
| | | Before ischemia | 7 days after ischemia | Before ischemia | 7 days after ischemia |
| Normal | 4 | 174 ± 8 | 175 ± 11 | 0.137 ± 0.006 | 0.138 ± 0.009 |
| Diabetes mellitus | 6 | 177 ± 6 | 191 ± 5** | 0.139 ± 0.005 | 0.149 ± 0.004** |
| Diabetes mellitus given 860 | 4 | 157 ± 6 | 158 ± 2 | 0.123 ± 0.005 | 0.124 ± 0.001 |

**P < 0.01 vs. "value before ischemia".

2. Results

Figure 3:
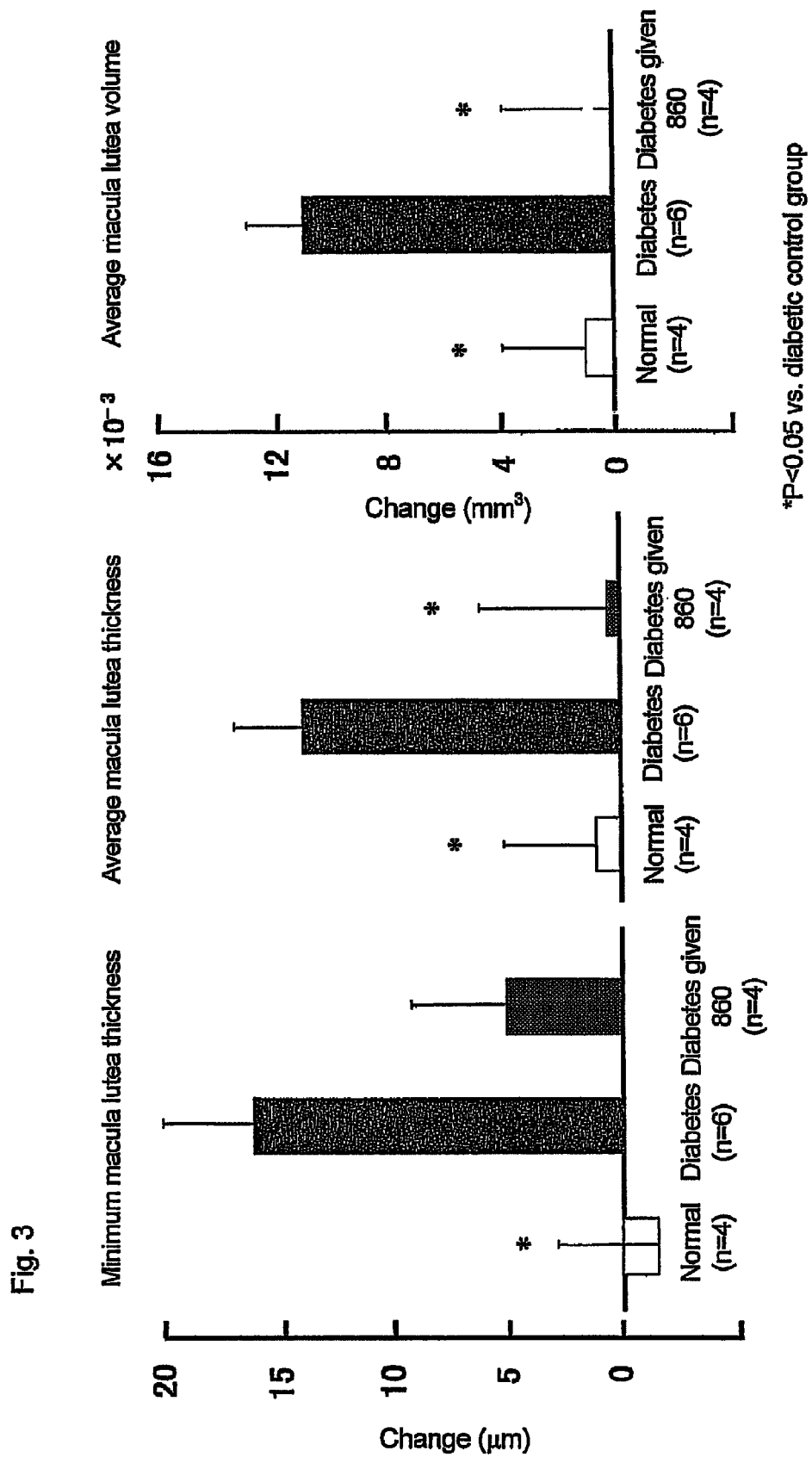
FIG. 3 shows a change in the minimum thickness, average thickness and average volume of macular central fovea in an ischemic/re-perfused eye in Efficacy Pharmacological Test Example 3.

The results are shown in Table 1 and FIG. 3. In the normal control group, formation of edema was not observed, and the thickness and volume (average) of the macular central fovea after ischemia and reperfusion were the same before the treatment and 7 days after the treatment. In the diabetic control group, on the other hand, an increase in the thickness and volume of the macular central fovea was observed 7 days after the treatment, and formation of edema was confirmed ($p<0.01$). This change was significantly increased as compared with that of the normal control group ($p<0.05$). In the diabetic group given 32 mg/kg SNK-860, formation of edema or its change was not observed similarly to the normal control group. These results show that SNK-860 inhibits edema formation under diabetes in the macular central fovea.

Efficacy Pharmacological Test Example 4

Clinical Results

1. Method

Among patients with diabetic maculopathy, 10 patients with diabetic macular edema having a retinal thickening or a hard exudates in a posterior pole of the retina were subjects. SNK-860 was orally administered in a dose of 30 mg (2 tablets each containing 15 mg SNK-860) once a day before breakfast for 8 weeks. During this test period, simultaneous use of eparlestat, intravitreal injection and sub-Tenon injection of an adrenal cortical hormone, and photocoagulation and vitrectomy were prohibited. Basic therapy of diabetes mellitus was carried out so as to give good blood glucose control throughout the test period.

Evaluation was carried out in terms of the thickness of the macular central fovea (in the diameter range of 1 mm from the center of macula lutea) and the thickness at the center of the central fovea measured by optical coherence tomography (OCT, Carl Zeiss), as well as corrected visual acuity (Log MAR).

Log MAR (Log Minimum Angle of Resolution) is one kind of logarithmic visual acuity, which is visual acuity expressed in logarithmic minimum angle of resolution. Decimal visual acuity 1.0 used frequently in Japan is 0.0 in terms of Log MAR, and decimal visual acuity 0.1 is 1.0 in Log MAR. A log MAR visual acuity of 0.1 to 0.5 corresponds to a decimal visual acuity of 0.8 to 0.32.

TABLE 2

Macula lutea thickness (μm) and corrected visual acuity (Log MAR) (mean ± standard deviation)

| | When initiated | Week 8 | P value |
|---|---|---|---|
| Center of central fovea | 323.1 ± 111.4 | 298.7 ± 90.6 | 0.0808 |
| Central fovea (diameter: 1 mm) | 324.3 ± 87.7 | 300.4 ± 74.4 | 0.0493 |
| Corrected visual acuity | 0.30 ± 0.22 | 0.24 ± 0.20 | 0.0917 |

TABLE 3

Corrected visual acuity (eye number)

| 2-stage improvement | 1-stage improvement | Unchanged | 1-stage deterioration |
|---|---|---|---|
| 3 | 2 | 6 | 1 |

Figure 4:
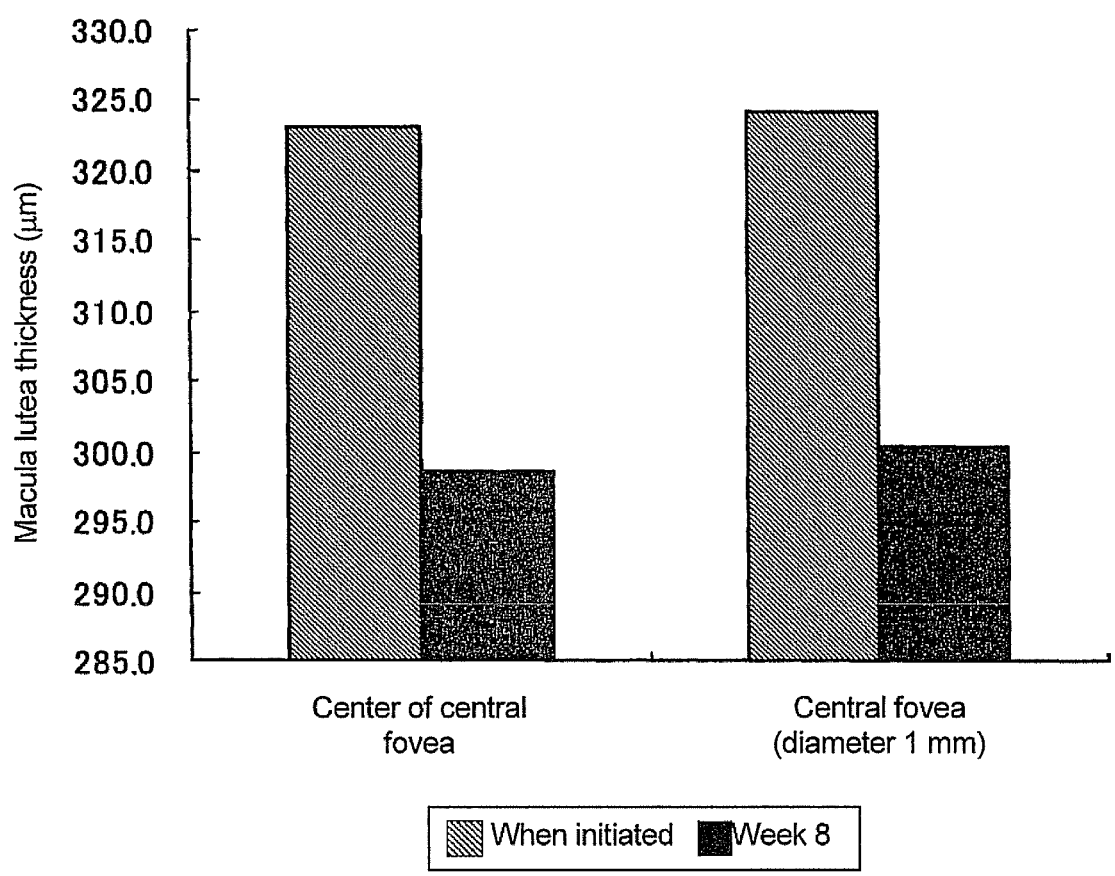
FIG. 4 shows the thickness of a macula lutea in a macular central fovea (diameter: 1 mm) and in the center of the central fovea before and after administration in Efficacy Pharmacological Test Example 4.
Figure 5:
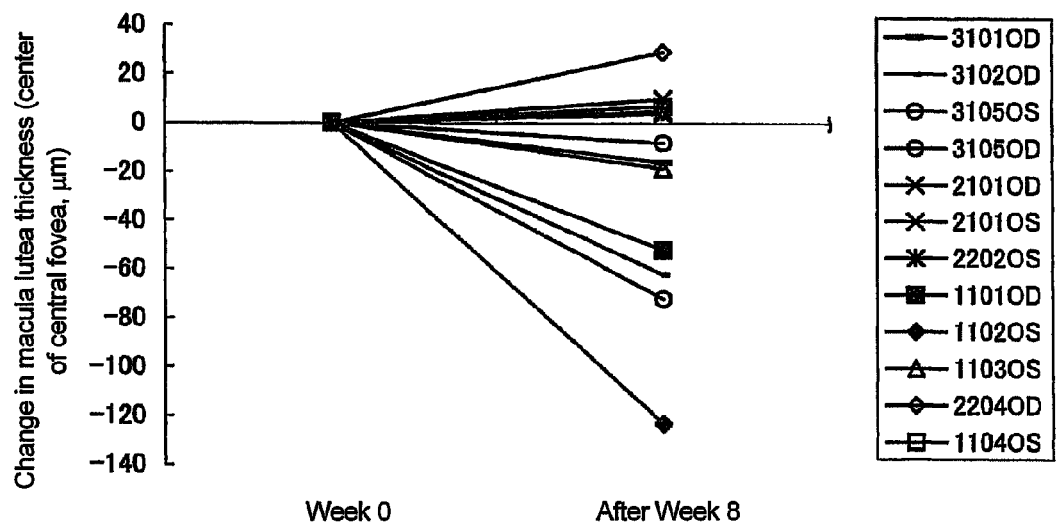
FIG. 5 shows a change in the thickness of a macula lutea in individual eyes (upper graph, in the center of a central fovea; lower graph, in the central fovea in the diameter range of 1 mm) before and after administration in Efficacy Pharmacological Test Example 4. A number in the example indicates identification number of the case, and alphabets OS and OD refer to left and right eyes, respectively.
Figure 5:
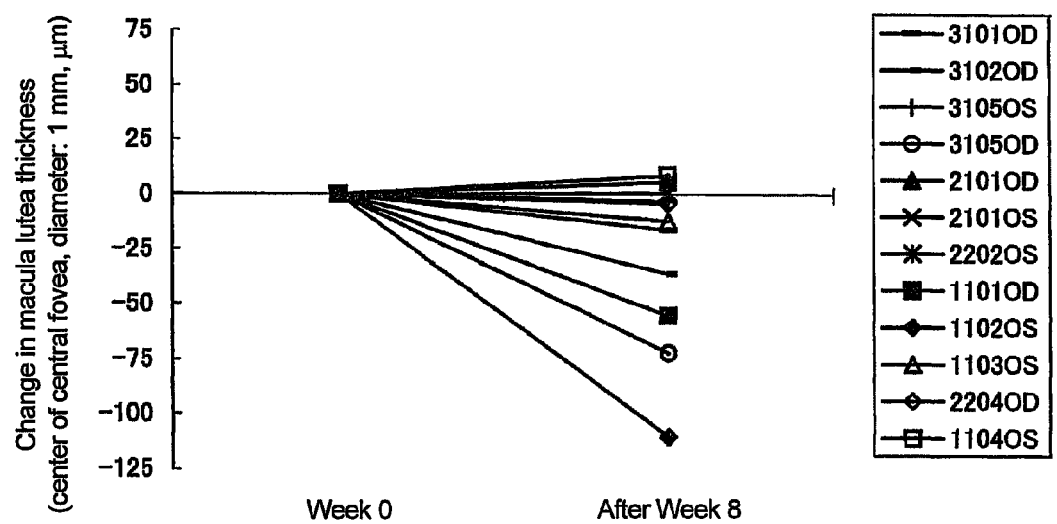

2. Results 12 eyes in the 10 cases were evaluated. When the test was initiated, the thickness of the macular central fovea (in the diameter range of 1 mm) was 324.3 μm on average, and the thickness at the center of the central fovea was 323.1 μm on average. After 8 weeks, these were reduced 300.4 μm and 298.7 μm respectively (Table 2, FIG. 4). A change in the thickness of macula lutea in the individual evaluated eye is shown in FIG. 5. These results show that the thickness of the macula lutea or the portion corresponding to the macula lutea in the model animal was also confirmed similarly in humans.

Figure 6:
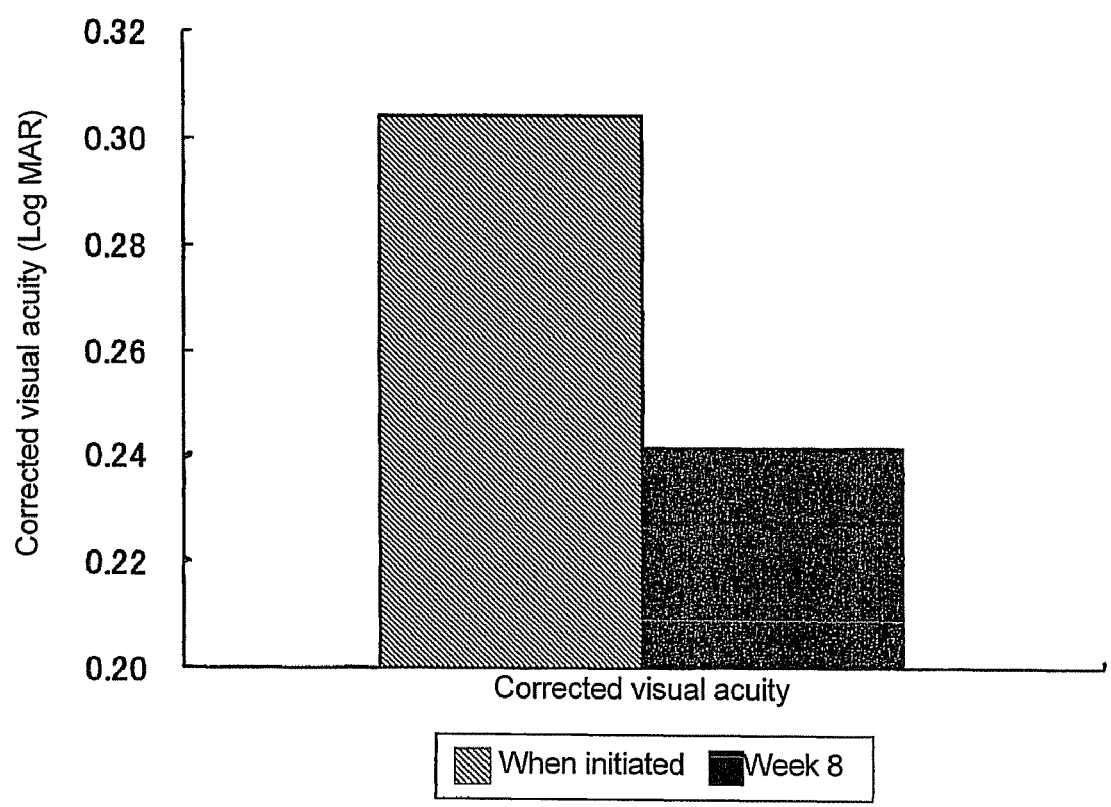
FIG. 6 shows corrected visual acuity before and after administration in Efficacy Pharmacological Test Example 4.

Out of the 12 eyes, 2-stage development with respect to corrected visual acuity was recognized in 3 eyes, 1-stage development in 2 eyes, and deterioration in only 1 eye (Table 3). The corrected visual acuity (Log MAR) on average was improved from 0.30 to 0.24 (FIG. 6). It was thus revealed that SNK-860 has a visual acuity-improving action important in therapy of maculopathy.

Diabetic maculopathy according to conventional findings is a gradually worsening disease that is considered difficult to treat. In contrast, the results of the present examples indicate that SNK-860 is effective for diabetic maculopathy. With respect to safety, no particularly problematic side effects were recognized.

What is claimed is:

1. A method for treating diabetic macular edema comprising administering to a subject in need thereof an effective amount of a compound represented by the following general formula:

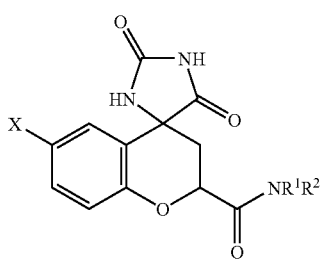

wherein X represents a halogen or a hydrogen atom, and $R^1$ and $R^2$ concurrently or differently represent a hydrogen atom or a C1 to C6 alkyl group.

2. The method for treating diabetic macular edema according to claim 1, wherein the compound is (2S,4S)-6-fluoro-2',5'-dioxospiro[chroman-4,4'-imidazolidine]-2-carboxamide.

3. The method for treating diabetic macular edema according to claim 1, wherein the diabetic macular edema is diffuse macular edema.

4. The method for treating diabetic macular edema according to claim 1, wherein the method causes an improvement in visual acuity or inhibition of a deterioration of visual acuity in a subject having diabetic macular edema.

5. A method for improving visual acuity or inhibiting a deterioration of visual acuity in a subject having diabetic macular edema comprising administering to the subject in need thereof an effective amount of a compound represented by the following general formula:

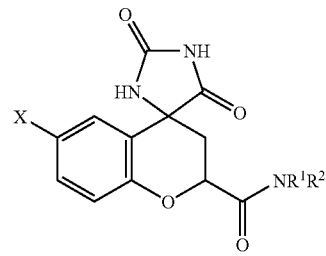

wherein X represents a halogen or a hydrogen atom, and $R^1$ and $R^2$ concurrently or differently represent a hydrogen atom or a C1 to C6 alkyl group.

6. The method for improving visual acuity or inhibiting a deterioration of visual acuity according to claim 5, wherein the compound is (2S, 4S)-6-fluoro-2', 5'-dioxospiro[chroman-4,4'-imidazolidine]-2-carboxamide.

* * * * *